United States Patent [19]

Kennedy et al.

[11] Patent Number: 4,956,273

[45] Date of Patent: Sep. 11, 1990

[54] SYNTHETIC PEPTIDES AND METHOD OF USE FOR DIAGNOSIS AND VACCINATION FOR AIDS AND ARC

[75] Inventors: Ronald C. Kennedy, San Antonio; Gordon R. Dreesman, Helotes, both of Tex.; Myron Essex, N. Easton, Mass.

[73] Assignees: Southwest Foundation For Biomedical Research, San Antonio, Tex.; President and Fellows of Harvard College, Cambridge, Mass.

[21] Appl. No.: 331,052

[22] Filed: Mar. 28, 1989

Related U.S. Application Data

[63] Continuation of Ser. No. 203,609, Jun. 2, 1988, abandoned, which is a continuation of Ser. No. 790,830, Oct. 24, 1985, abandoned.

[51] Int. Cl.[5] .................. G01N 33/569; A61K 39/12; C07K 7/08; C07K 7/10
[52] U.S. Cl. ........................................ 435/5; 530/324; 530/325; 530/403; 530/826; 424/87; 435/7; 436/811
[58] Field of Search ............... 435/5, 7; 530/324, 325, 530/403, 826; 424/89

[56] References Cited

U.S. PATENT DOCUMENTS

| | | | |
|---|---|---|---|
| 4,117,113 | 9/1978 | Allison et al. | 424/89 |
| 4,474,757 | 10/1984 | Arnon et al. | 424/89 |
| 4,591,552 | 5/1986 | Neurath | 435/7 |
| 4,629,783 | 12/1986 | Cosand | 530/324 |
| 4,689,204 | 8/1987 | Buck | 422/100 |
| 4,734,362 | 3/1988 | Hung | 435/68 |
| 4,743,678 | 5/1988 | Essex | 435/5 |

OTHER PUBLICATIONS

Ratner et al., Nature, 312 (1/24/85) 277–83.
Crowl et al., Cell, 41 (7/1985) 979–86.
Allan et al., Science, 288 (5/31/85) 1091–4.
Schupbach et al., New. Eng. J. Med, 312 (1/31/85) 265–70.
Montagnier et al, Virology, 144 (1985) 283–9.

Primary Examiner—Christine Nucker
Attorney, Agent, or Firm—Cox & Smith

[57] ABSTRACT

Composition and method for detection of and vaccination against the viral causative agents of AIDS and ARC. The composition is a synthetic peptide, the amino acid sequence of which is sufficiently homologous to the amino acid sequence of the gp 41 and gp 120 subunits of the gp 160 envelope glycoprotein of HTLV-III, LAV or ARC to produce an immunogenic response in a patient and which has a hydrophilic region therein. The composition may be conjugated to an appropriate carrier for use as a vaccine against AIDS and ARC or bound to the ligand of a specific binding pair, contacted with a sample of biological fluid from a patient suspected of having contracted AIDS or ARC and thereafter contacted with the anti-ligand of the specific binding pair for detection of any antibodies against the viral causative agents of AIDS or ARC which may be present in the sample.

8 Claims, 4 Drawing Sheets

| AA# | AA CODE | H VALUE | H AVERAGE |
|---|---|---|---|
| 1 | K--LYS | 3 | -.3 |
| 2 | E--GLU | 3 | -1.183 |
| 3 | Y--TYR | -2.3 | -1.183 |
| 4 | A--ALA | -.5 | -1.1 |
| 5 | F--PHE | -2.5 | -.517 |
| 6 | F--PHE | -2.5 | -.4 |
| 7 | V--TYR | -2.3 | -.283 |
| 8 | K--LYS | 3 | .1 |
| 9 | L--LEU | -1.8 | -.7 |
| 10 | D--ASP | 3 | .1 |
| 11 | I--ILE | -1.8 | -.367 |
| 12 | I--ILE | -1.8 | .433 |
| 13 | P--PRO | 0 | .667 |
| 14 | I--ILE | -1.8 | .6 |
| 15 | D--ASP | 3 | .95 |
| 16 | N--ASN | .2 | |
| 17 | D--ASP | 3 | |
| 18 | T--THR | -.4 | |
| 19 | T--THR | -.4 | |
| 20 | S--SER | .3 | |

PEAK VALUES ARE:

| PEAK # | AA POS. | AVE VALUE |
|---|---|---|
| 1 | 15 | .95 |
| 2 | 8 | .1 |

HYDROPHILICITY PLOT

P - PROLINE
O - WHERE MORE THAN ONE AROMATIC AA
(TYR, TRP, HIS) OCCUR IN THE
SEQUENCE

SYNTHETIC PEPTIDES AND METHOD OF USE FOR DIAGNOSIS AND VACCINATION FOR AIDS AND ARC

STATEMENT OF GOVERNMENT INTEREST

The invention herein was made with Government support and the Government has certain rights in the invention.

This application is a continuation of co-pending application Ser. No. 06/790,830, filed on Oct. 24, 1985.

BACKGROUND OF THE INVENTION

The present invention relates to a vaccine for the prevention of acquired immunodeficiency syndrome (AIDS) and AIDS-related complex (ARC). In particular, the present invention relates to a synthetic peptide which may be used in a method of immunization against AIDS and in a diagnostic assay for AIDS.

AIDS was first discovered as a severe immune deficiency which resulted in reports of opportunistic infections occuring among male homosexuals (see Gottlieb, M.S., et al., 305 N. Engl. H. Med. 1425–1431 (1981) and Masur, H., et al., 305 N. Engl. J. Med. 1431–1438 (1981)). The incidence of this new human disease, named "acquired immunodeficiency syndrome" (AIDS), is rapidly growing. Although sexual transmission appears to be the primary mode of transfer, a number of cases in which the disorder was transferred by blood transfusion have been reported (see Gottlieb, et al., supra). The etiologic agent of this disease has been shown to be a human retrovirus, known variously as human T lymphotropic virus type III (HTLV III), lymphadenophathy-associated virus (LAV)(Barre-Sinoussi, F., et al., 220 Science 868–871 (1983)), or AIDS-associated retrovirus (ARV).

Seroepidemiological studies have identified HTLV-III—specific antibodies in the serum of most patients with AIDS or ARC. The predominant antigens recognized by antibodies in sera obtained from AIDS patients and from hemophiliacs are associated with the envelope glycoproteins. Further, the most immunogenic proteins of the human T lymphotrophic viruses, HTLV-I and HTLV-II are cell surface-expressed glycoproteins (Chen, I.S. et al., 305 Nature (London) 502 (1983)).

The envelope (env) gene product of HTLV-III is synthesized as a polyprotein precursor and is subsequently glycosylated within infected cells This glycosylated glycoprotein, with an estimated molecular weight of 160K (gp 160) is processed into gp 120 and gp 41 subunits. The gp 110 glycoprotein of LAV appears to be the same protein as gp 120. This gp 41 subunit is one of the predominant polypeptides in purified virus preparations.

Antibodies from AIDS and ARC patients contain viral neutralizing activity; however, infection presumably occurred in those patients prior to the development of neutralizing antibody. The general notion with retroviruses is that the antigenic determinants or epitopes associated with the induction of neutralizing antibodies are associated with the glycoprotein envelope (see Holden, H.T. and T. Taniyama, 150 J. Exp. Med. 1367 (1979) and Flyer, D.C. et al., 305 Nature (London) 815 (1983)). As will be described, it has now been demonstrated that the gp 41, gp 120 and gp 160 envelope glycoproteins are the most immunogenic epitopes in virus-exposed individuals. The present invention is premised upon the assumption that the critical epitopes involved in the induction of protective virus neutralizing antibody are associated with the two viral envelope glycoprotein subunits, gp 120 and gp 41.

SUMMARY OF THE INVENTION

An object of the present invention is to provide a vaccine which will immunize patients against AIDS and ARC. This object has been accomplished by preparing a synthetic peptide which elicits a protective antibody response in the immunized subject which resides in the idiotypic specificity of the antibodies against those peptides. In order to accomplish this object, it was first necessary to identify a number of synthetic peptide candidates capable of eliciting such a response. It is, therefore, also an object of the present invention to characterize the amino acid sequence of the most immunogenic proteins of HTLV-III (i.e., gp 120 and gp 41), identify the structural conformation of those proteins and the portions of the amino acid sequence which represent the most likely antibody binding sites, and then synthesize synthetic peptides with that same sequence and structure, or with a sequence and structure which is sufficiently homologous to the portion of the sequence which represents the binding site as to also be immunogenic.

It is another object of the present invention to provide an assay for the diagnosis of AIDS or ARC.

It is another object of the present invention to provide an assay for the detection of antibodies against HTLV-III in those individuals suspected of having AIDS or ARC.

It is another object of the present invention to produce idiotype antibodies to the gp 120 and gp 41 envelope glycoproteins of HTLV-III using synthetic peptides.

It is another object of the present invention to provide a composition for use in vaccination against AIDS and/or ARC comprising an immunogenic synthetic peptide and a carrier.

Another object of the present invention is to provide a method of screening other putative vaccine candidates against AIDS and/or ARC.

Another object of the present invention is to provide a method of serotyping viral isolates from AIDS and ARC patients.

It is another object of the present invention to elicit the production of antibodies capable of neutralizing and/or destroying the HTLV-III virus in humans.

These, and other objects which will be clear to those skilled in the art from the following detailed description, have been accomplished by providing a synthetic peptide useful in producing an immunogenic response to the viral causative agents of AIDS or ARC comprising a chain of amino acids having a sequence homologous to the gp 120 or gp 41 subunits of the gp 160 precursor of the envelope glycoprotein of HTLV-III, LAV or ARV and having a hydrophilic region therein.

The present invention is also directed to a composition of matter for use in vaccination against the viral causative agents of AIDS and ARC comprising a synthetic peptide made up of an amino acid sequence homologous to the gp 120 or gp 41 subunits of the gp 160 precursor of the envelope glycoprotein of HTLV-III, ARV or LAV and having a hydrophilic region therein and a carrier.

The present invention is also directed to a method of immunizing against the viral causative agents of AIDS comprising administering an immunogenically effective amount of a synthetic peptide to an animal, the synthetic peptide being comprised of an amino acid sequence homologous to the gp 120 or gp 41 subunits of the gp 160 precursor of the envelope glycoprotein of HTLV-III, ARV or LAV.

DETAILED DESCRIPTION OF THE INVENTION

Figure 1:
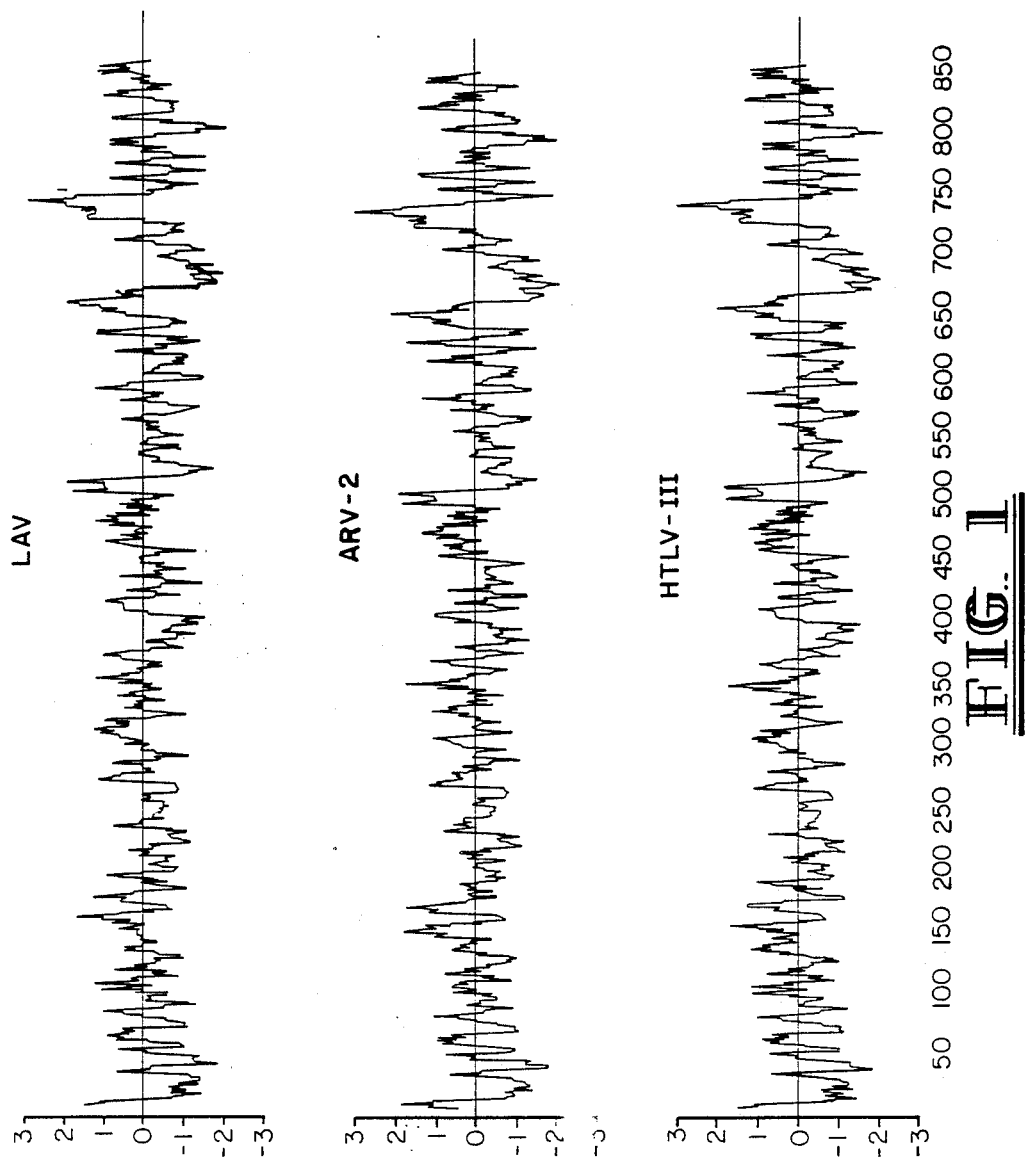
FIG. 1 is an artist's rendition of the plot of the hydrophilic averages for each residue against the amino acid sequence of the gp 160 precursor glycoprotein of the gp 120 and gp 41 env glycoproteins of HTLV-III, LAV and ARV generated by a computer program utilizing the Chou-Fasman predictive scheme for secondary structure.

As noted above, the present invention is based upon the assumption that it is the gp 120 and gp 41 subunits of the envelope glycoprotein which are the most immunogenic epitopes of the viral causative agents of AIDS and ARC. As will be described, the accuracy of that assumption has now been verified. It was next necessary to determine the sequence of amino acids of the gp 120 and gp 41 subunits and to select the portions of those envelope glycoprotein subunits which represent the most likely antibody-binding sites. This selection was accomplished by means of computer modeling of the structure of the gp 120 and gp 41 subunits.

Once the most likely sites were identified, chains of amino acids were synthesized to duplicate the amino acid sequence at each of those sites. Those chains of amino acids, called synthetic peptides, were then used to induce an immune response in rabbits, and the rabbit anti-peptide antibody tested to verify that it binds to the viral causative agents of AIDS and ARC. Those synthetic peptides which induce rabbit antibodies which bind to AIDS virus are then tested for their ability to bind human anti-HTLV-III antibody, and the rabbit anti-HTLV-III antibodies are also tested to determine whether they are capable of neutralizing the infection virus in tissue culture. Once the most immunogenic synthetic peptides which fulfill those criteria are identified, they are used for both a vaccine and as a diagnostic assay to identify individuals exposed to the viral causative agents of AIDS and ARC as well as AIDS and ARC patients.

The amino acid sequence of the gp 120 and gp 41 subunits was determined by prediction based upon the nucleotide sequence of HTLV-III and the verification of those sequences by analysis of the sequence of the NH$_2$-terminus by Edman degradation of the proteins labeled with $^3$[H]leucine and $^{35}$[S]cystine, as well as $^3$[H]valine.

Verification of the immunogenic nature of the gp 120 and gp 41 (and their precursor, gp 160) envelope glycoproteins was obtained by screening serum samples from AIDS and ARC patients to identify those with antibodies against HTLV-III by indirect cell membrane immunofluorescence (MIF) using the H9/HTLV-III cell line and by radioimmunoprecipitation and sodium dodecylsulfate-polyacrylamide gel electrophoresis (RIP/SDS-PAGE) with $^{35}$[S]cystine-labeled H9/HTLV-III cells. Representative antibody-positive sera were also tested on glycoprotein preparations of H9/HTLV-III cells enriched through the use of a lentil lectin column. The results indicated that the highest percentage of antibody-positive sera contained antibodies which recognized gp 120 and gp 160 and that all of the samples which contained antibodies to other epitopes also contained antibodies which recognized gp 120 and gp 160.

Selection of the most immunogenic sites on the gp 120, gp 41 and gp 160 envelope glycoproteins was accomplished by modifying a computer program based on the hydrophilicity index described by Hopp, T.P. and K.R. Woods (78 Proc. Nat'l Acad. Sci. USA 3824–3828 (1981)) to predict the location of the hydrophilic regions associated with the HTLV-III envelope gp 160 glycoprotein from HTLV-III, LAV and ARV. The amino acid sequence of those glycoproteins was also analyzed for secondary structure using the Chou-Fasman predictive scheme (Chou, P.Y. and E.D. Fasman, 13 Biochemistry 222 (1974)). The peak hydrophilic areas were compared with the predicted secondary structure, and those areas most likely to be exposed on the surface of the glycoprotein were identified. Those areas were also examined for the presence of a β turn because previous studies using viral envelope proteins had indicated that the hydrophilic regions exposed on the surface with predicted β turn secondary structure represent immunogenic surface regions on the virus (Dreesman, G.R., et al., 295 Nature (London) 158–160 (1982)(hepatitis B surface antigen); Hopp and Woods, supra (hepatitis B surface antigen); Henderson, L.E., et al., 256 J. Biol. Chem. 8400–8406 (1982) (Raucher murine leukemia virus); Gingeras, T.R., et al., 257 J. Biol. Chem. 13475–13491 (1983)(adenovirus spike protein); Watson, R.J., et al., 218 Science 381–384 (1982)(herpes simplex virus envelope glycoprotein D)).

Having identified the sequence of the gp 160 glycoprotein from HTLV-III, LAV and ARV and the regions in that sequence which are likely to be immunogenic, the next step was to synthesize a polypeptide with the same amino acid sequence (or a sequence which is similar enough so as to be treated in the same manner by the antibody which binds with that epitope) as that region of the glycoprotein. The synthesis was carried out by solid-phase methodology on a Biosearch Sam II peptide synthesizer. A total of six synthetic peptides were synthesized, each selected on the basis of the above-described tests for predicted immunogenicity. The amino acid sequences of each of those synthetic peptides is given in Table II.

The six synthetic peptides were then used to induce an immune response in rabbits by coupling the peptides to a suitable carrier and injecting the rabbits with the synthetic peptides/carrier, and the antibody titer of the rabbit sera was tested by the ability of the antibody to bind with the peptide conjugated to bovine serum albumin (BSA). Those results were confirmed by conducting inhibition studies in which the inhibition of the binding of the rabbit anti-peptide to the peptide-BSA was measured.

The rabbit anti-peptide antibodies were then examined for their ability to recognize the native proteins associated with HTLV-III. An HTLV-III infected T-cell line labelled with $^{35}[S]$-cystine was used for immunoprecipitation to determine whether the anti-peptide sera would bind any radioactively labelled HTLV-III native proteins. Autoradiography with SDS-PAGE confirmed that the rabbit anti-peptide antibodies specifically precipitated a single protein which corresponded to the gp 160 precursor envelope glycoprotein gp 160 of HTLV-III. The precursor gp 160 product is cleaved to yield the major gp 120 envelope glycoprotein and gp 41, the transmembrane glycoprotein. The other envelope subunit, gp 41, does not radioactively label to the same degree with $^{35}[S]$-cystine as the amino end of the precursor gp 160 glycoprotein, and was not detected by immunoprecipitation. However, when when $^{35}[S]$-methionine was used as a label, the binding was detected by immunoprecipitation, a result which has been confirmed using Western transfer methods.

The anti-peptide antibodies thus generated are then tested to determine whether they are capable of neutralizing the viral causative agents of AIDS or ARC. The neutralizing ability of the anti-peptide antibodies was tested by incubating purified virus and rabbit anti-peptide antibodies with infected MOLT-3 cells, then examining the lysed cells by Western transfer and immunoprecipitation for the presence of the virus. Once the most immunogenic synthetic peptides are identified, they are used for both a diagnostic assay for AIDS and ARC and as a vaccine.

When used as a diagnostic assay, the preferred method relies upon the detection of antibody against the viral causative agent of AIDS and/or ARC. This assay is conducted, for instance, by coating an insoluble matrix such as a column of polystyrene beads or micro well test plate with a synthetic peptide or a synthetic peptide coupled to a carrier protein (i.e., bovine serum albumin) containing the amino acid sequence associated with the epitope(s) of one of the viral causative agents of AIDS or ARC. Alternatively, the insoluble matrix may be coated with a number of difference synthetic peptides (a "cocktail") containing the amino acid sequence of several epitopes. A sample of biological fluid from the suspected patient is incubated with the synthetic peptide-coated matrix to immunocapture the predetermined antibody. The resultant matrix, separated from the uncaptured sample, is then incubated with a quantity of biotin-labeled antibody directed to the species of the predetermined antibody (e.g., anti-human antibodies would be the predetermined antibody if the body fluid is taken from a human patient) sufficient to bind a measurable number of human antibodies, if present. The resultant matrix, separated from uncaptured biotin-labeled antibody and the matrix, is then incubated with a quantity of labeled avidin, preferably avidin labeled with an enzyme such as alkaline phosphatase, sufficient to bind a measurable number of antibodies, if present. The resultant matrix is separated from uncaptured avidin and a label detected and/or preferably quantified by adding the substrate which is specific for that enzyme to thereby determine indirectly the presence of antibody to AIDS virus in the sample. The antibody could also be labeled with an enzyme directly, in which case the matrix is incubated with an enzyme-reactive substrate, and the change in the substrate, e.g., a color change or fluorescence emission is detected. Regardless of whether the label is an antibody, an enzyme or an enzyme labeled with biotin-avidin, the binding pair formed by the antigen and antibody or the enzyme and substrate will be referred to as the "ligand" and "antiligand" of the specific binding pair.

A diagnostic assay could also be designed for detection of the antigen rather than the predetermined antibody. To conduct an antigen test, the solid phase matrix is coated with antibodies to the viral causative agents of AIDS, i.e., the antibodies produced by immunization with a synthetic peptide (or, preferably, several peptides) such as the peptides of the present invention. The sample of biological fluid from a patient suspected of having been infected with the AIDS virus is then added to the matrix, followed by the addition of biotin-labeled antibody, where the antibody is an antibody which binds to the AIDS virus produced in the same way as discussed above. The avidin-labeled enzyme is then added, followed by the substrate specific for the enzyme, and the color change or fluorescence emission is detected. Either of these assays could also be conducted as an inhibition assay where, instead of adding biotin-labeled antibody to the AIDS virus to the bound antigen, a biotin-synthetic peptide conjugate is added.

To use the synthetic peptides of the present invention as a vaccine against the viral causative agents of AIDS, approximately 100 to 1000 micrograms of synthetic peptide, or several synthetic peptides, prepared according to the teachings of the present invention is coupled to an appropriate carrier, and administered to an individual with an adjuvant. Appropriate carriers include the toxoid components, any one of several large protein-containing substances which are foreign to the animal to be vaccinated, any of several small peptide preparations which have demonstrated adjuvant activity and which behave as a carrier, or liposomes. The toxoid components could be tetanus toxoid or diptheria toxoid. The phrase "large protein-containing substances which are foreign to the animal to be vaccinated", refers to such substances as Keyhole limpet hemocyanin (KLH) or BSA. The small peptide preparations with demonstrated adjuvant activity which also act as a carrier include muramyldipeptide, murabutidine, and the polyamino acids such as poly-L-glutamic acid or poly-L-lysine. Approximately 10 to 100 molecules of synthetic peptide is complexed to each molecule of carrier using a heterobifunctional cross-linker, such as m-maleimidobenzyl-N-hydroxysuccinimide ester (MBS) (Liu, F.T., et al., 18 Biochemistry 690 (1979), Green, N. et al., 28 Cell 477 (1982)), glutaraldehyde, a carbdiimide succinyl anhydride or N-succinimidyl-3-[2-pyridyldithio]-propionate.

Suitable adjuvants include alum (aluminum hydroxide) and any of a number of additional adjuvants such as are known to those skilled in the art. The carrier-synthetic peptide complex may be administered in a pharmaceutically acceptable diluent such as distilled water, phosphate buffered saline, citrate buffer or any neutral pH buffer, i.e. a buffer with a pH of between about 6 and about 8.

The synthetic peptides of the present invention may also be used to screen putative vaccine candidates against AIDS and/or ARC. Such screening may best be conducted by coating an insoluble matrix with a synthetic peptide or with the synthetic peptide coupled to a carrier protein. The vaccine candidate is then incubated with antibodies against the peptide (with or without biotin) such as a 1:1000 dilution of IgG-rabbit anti-peptide-biotin antibody If biotin labeled antibody is used, the avidin-enzyme conjugate is added (if no biotin is used, add biotin-labeled anti-species (such as biotin-labeled goat anti-rabbit IgG) antibody, then add avidin-enzyme), the substrate is then added and the reaction detected.

The synthetic peptides of the present invention may also be used to serotype viral isolates from AIDS or ARC patients. Sero-typing is conducted in the same manner as described above for screening vaccine candidates, because in both cases, the anti-peptide antibody must bind with the intact AIDS viral causative agent. However, in the case of the serotyping of the viral isolate, a portion of the isolate is added, in serial fashion, to a number of bound anti-peptide antibodies, each antibody being specific for a different synthetic peptide and having been bound to a separate insoluble matrix.

The present invention may be better understood by reference to the following non-limiting examples.

EXAMPLE 1.

Maintenance and Radioactive Labeling of HTLV-III Infected Cells

Two HTLV-III producing cell lines, H-9 and MOLT-3, were grown in RPMI-1640 supplemented with 20% fetal bovine serum, 2 mM glutamine, non-essential amino acids and 0.1% NaHCO$_3$ (maintenance medium). Cell cultures were labeled by transferring cells from maintenance medium to cystine and glucose deficient medium for 1 hour before adding $^{35}$[S]-cystine (150 μCi/ml) and $^3$[H]-glucosamine (20 μCi/ml for 24 hr). Cells were separated from tissue culture supernatants by low speed centrifugation (1,000×g for 10 minutes).

EXAMPLE 2.

Verification of Immunogenicity of gp 120 and gp 41 Subunits of HTLV-III

Serum samples taken from subjects who came to a community health clinic in a high-risk area for AIDS and ARC and to hospitals in that area during 1983 and 1984 were screened for antibodies to HTLV-III by indirect cell membrane immunofluorescence (MIF) using the H9/HTLV-III cell line as described by Essex, et al., 320 Science 859 (1983). Briefly, this method involves separating the cells from the media as described in Example 1, above, washing between 1×10$^6$ and 2×10$^6$ cells twice with phosphate buffered saline (PBS), and exposing them to 40 μl of a 1:4 dilution of previously centrifuged serum for 30 minutes at 37° C. Each preparation was then washed twice with PBS and reacted with 40 μl of a 1:20 dilution of fluorescein conjugated F(ab')$_2$ fragment of goat antiserum to human immunoglobulins (IgA+IgG+IgM) (Cappel, Cochranville, Pa.). The samples were again incubated at 37° C. for 30 minutes, washed twice with PBS, and examined by fluorescence microscopy. If at least 50 percent (or 40 percent when indicated) of the cells showed specific fluorescence, the serum samples were judged positive. Samples were coded and read in a double blind manner, and positive and negative human serum samples were included as a reference. The results of this screening are presented in Table I.

All of the samples from the same 190 individuals were also tested by radioimmunoprecipitation and sodium dodecyl sulfate-polyacrylamide gel electrophoresis (RIP/SDS-PAGE) with $^{35}$[S]cystine-labeled H9/HTLV-III and uninfected H9 cells (Essex, et al., supra). Briefly, this method is as follows. After disruption of the labeled cells with RIPA buffer (0.15 M NaCl, 0.05 M tris-HCl, pH 7.2, 1% Triton X-100, 1% sodium deoxycholate, and 0.1% SDS), cells were centrifuged at 100,000×g for one hour. The lysate supernatant was cleared once with 10 μl of reference negative control serum bound to Protein A-Sepharose CL-4B (Protein A beads) before portions were reacted with 10 μl of the human test sera. Immunoprecipitates were eluted in a sample buffer (0.1 M Cleland's reagent, 2% SDS, 0.08 M tris-HCl, pH 6.8, 10% glycerol, and 0.2% bromophenol blue) by boiling at 100° C. for two minutes. Samples were analyzed in a 12.5% acrylamide resolving gel with 3.5% stacking gel according to the discontinuous buffer system of Laemmli (227 Nature (London) 680 (1970)). Surface-labeling was carried out by lactoperoxidase-catalyzed radioiodination. The results are presented in Table I.

Representative antibody-positive sera were also tested on glycoprotein preparations of H9/HTLV-III cells enriched through the use of a lentil lectin column HTLV-III glycoproteins were incubated with lentil lectin Sepharose 4B for four hours and then eluted with 0.2 M methyl mannoside. The resulting proteins were then immunoprecipitated with HTLV-III reference serum, and the precipitates bound to Protein A-Sepharose were dissociated from antibody by boiling for two minutes in the presence of 0.1% SDS and 0.15 M sodium citrate pH 5.5. Equal portions were then incubated for three hours at 37° C. in the presence or absence of 0.25 ug of endoglycosidase H. The reaction was terminated by the addition of five volumes of cold 95% ethanol, and the proteins were precipitated overnight at ×20° C. The samples were then centrifuged at 12000×g for 15 minutes and the proteins were reconstituted with electrophoresis sample buffer, boiled for three minutes, and subjected to electrophoresis. Samples from four antibody-positive AIDS patients precipitated proteins of about 120kD, 160kD and 41kD. Similar results were obtained with two antibody-positive ARC patients, and with two antibody-positive healthy homosexual males. No proteins of related sizes were detected in sera from antibody-negative healthy homosexual males or with sera from apparently healthy laboratory workers. None of the human serum samples tested contained antibodies to other epitopes on the HTLV-III virus without also containing readily detectible antibodies to at least gp 120 and gp 160.

TABLE I

| Category | Number Tested | Number (and percent) positive for | |
| --- | --- | --- | --- |
| | | HTLV-III-MAI[1] | gp120[2] |
| AIDS | 50 | 48(96) | 49(98) |
| ARC | 50 | 43(86) | 46(92) |
| HEALTHY HOMO-SEXUAL MALES | 73 | 34(47) | 36(49) |
| HEALTHY LABORATORY WORKERS | 27 | 0 | 0 |

[1] Assay for HTLV-III membrane antigens (HTLV-III-MA) conducted by MIF as described by Essex, et al., 220 Science 859 (1983).
[2] Assay for gp 120 envelope glycoprotein of HTLV-III conducted by RIP/SDS-PAGE as described by Essex, et al., 220 Science 859 (1983).

EXAMPLE 3.

Figure 2:
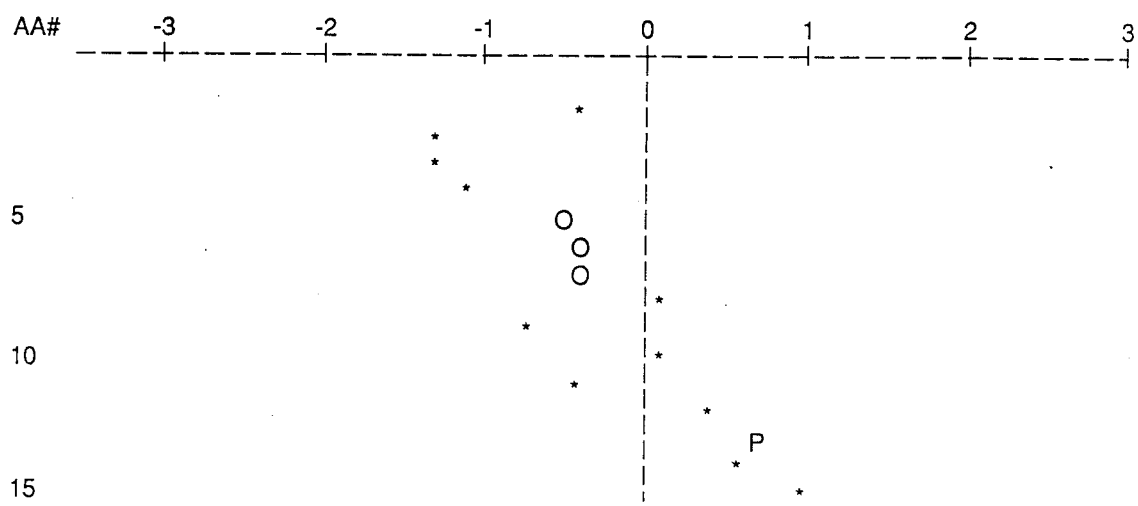
FIG. 2 is an actual computer plot of a segment of the amino acid sequence of the plot of FIG. 1.

Selection of Immunogenic Sites On gp 120, gp 41 and gp 160 Envelope Glycoproteins The predicted amino acid sequences of the gp 160 precursor glycoprotein from the three viral isolates HTLV-III, LAV and ARV were run through a computer program which utilizes the parameters and hydrophilic values arrived at by Hopp, T.P., and K.R. Woods (20 Mol. Immunol. 483-489 (1983)). The computer program was written in Apple BASIC. The program was written with the ability to save the amino acid sequence to disk in a format which is compatible with the Chou-Fasman predictive scheme (Chou, P.Y. and E. D. Fasman, 13 Biochemistry 222 (1974)). The hydrophilicity program calculates the hydrophilic averages over a hexapeptide length, thereby increasing the accuracy of the predictions. Since there are no hydrophilic values for Asx or Glx, the amide form of the acidic amino acid residues, those codes must be edited out before running the calculations. The plots of the hydrophilic averages per residue against the amino acid sequence number for the three AIDS viral glycoproteins are shown in FIG. 1. FIG. 1 is actually an artist's rendition of the computer graphical output of the hydrophilicity plots from the three viral causative agents of AIDS/ARC which have been characterized. The highest peak (most hydrophilic) is shown in a similar area for all three sequences, with the maximum hydrophilic index occuring at residues 739, 744, and 738 for HTLV-III, LAV and ARV respectively. The second highest hydrophilic region centers around the amino acid residues 653-659 just to the amino terminal side of peak 1. The third highest hydrophilic region was found to be in close proximity to peak 1, centered around amino acid residues 733-739 for each of the three glycoproteins. An actual computer graph output of a segment of the HTLV-III sequence is depicted in FIG. 2. Due to the length of the entire HTLV-III sequence, only a segment is shown. A proline residue is shown graphically as a "P". Two or more aromatic amino acids in a row within the sequence are depicted as an "0". The presence of aromatic amino acids within a given sequence is indicative of regions that possess a high degree of potential for hydrogen bonding. Thus, hydrogen bonds may act to influence the overall confirmation of the protein. These data indicate that these regions are likely to be exposed on the surface of the glycoprotein.

Figure 3:
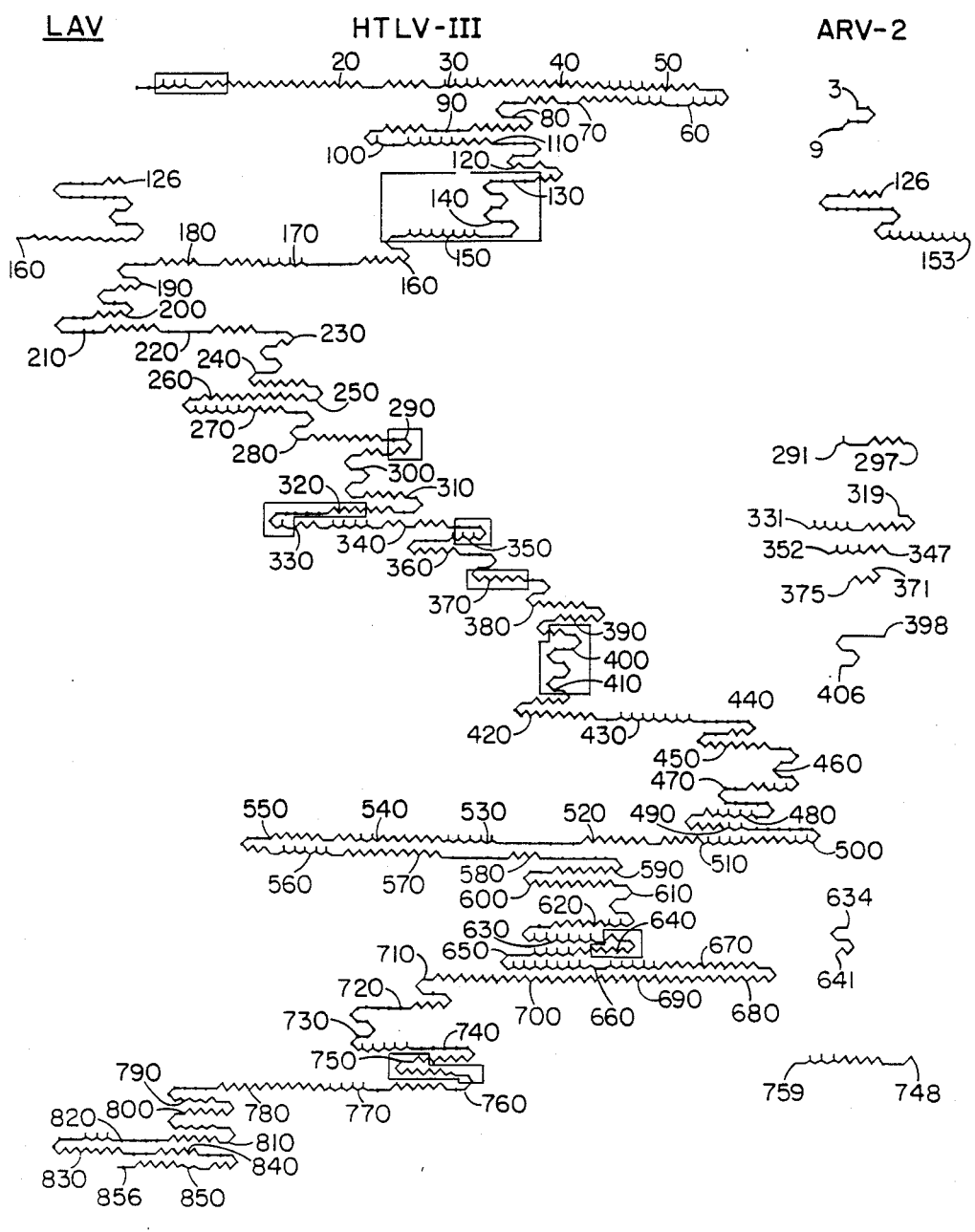
FIG. 3 is a schematic representation of the secondary structure of the amino acid sequence of the plot of FIG. 1 showing the differences between the secondary structure of the gp 160 precursor of HTLV-III, LAV and ARV.

The predicted secondary structure of the HTLV-III glycoprotein, as determined by the Chou-Fasman predictive scheme, is depicted in FIG. 3. The major differences in predicted secondary structure between HTLV-III, LAV and ARV are shown in boxed regions. These regions include residues 127-150, 127-155, and 126-148 for HTLV-III, LAV and ARV-II respectively, where the residue homology is only about 40%, causing changes in β turn potentional. In addition, significant differences were noted at regions 319-330 and 398-408 of ARV, 323-333 and 401-415 of LAV, and 318-328 and 396-411 of HTLV-III. Comparison of hydrophilicity with secondary structure indicates that peak 1 contains four potential β turns within the region, making the region centered around amino acids 739-744 a prime candidate as a potential antigenic determinant(s). Hydrophilic peak 2 also possessed a predicted β turn, suggesting that this region is exposed on the surface of the envelope glycoprotein.

EXAMPLE 4.

Peptide Synthesis

A synthetic peptide having the amino acid sequence shown under the Peptide 5 heading in Table II, which corresponds to the sequence of residue numbers 346 through 357 of the gp 120 glycoprotein of the viral causative agents of AIDS and ARC, was synthesized by solid-phase methodology (Merrifield, R.B., 32 Adv. Enzymol. 221 (1969)) on a Biosearch SamII peptide synthesizer. Butyloxycarbonyl-S-4-methylbenzyl-L-cystine coupled to polystyrene using dicyclohexylcarbodiimide with a catalytic amount of 4-N,N-dimethylaminopyridine was used as the solid-phase support for the synthesis. The four amino groups were protected with tert-butyloxycarbonyl (t-BOC) and the side chain protecting groups were as follows: benzyl ether for the hydroxyl of serine, dichlorobenzyl ether for the phenolic hydroxyl of tyrosine, and the and β benzylesters were used for the carboxyl groups on glutamic acid and aspartic acid, respectively. Trifluoroacetic acid (40% in $CH_2CL_2$) was used to remove t-BOC and the resulting salt was neutralized with N,N-diisopropylethylamine (10% in $CH_2CL_2$) Diisopropylcarbodiimide was used to couple the t-BOC amino acids. The specific steps of the synthesis are published in Sparrow, J.T., 41 J. Org. Chem. 1350 (1976), hereby incorporated in its entirety by this specific reference thereto.

The protecting groups were removed and the peptide was cleaved from the resin at 0° C. with anhydrous hydrogen fluoride containing 10% anisole and 1% ethanedithiol as scavengers. The hydrogen fluoride reagent was removed under vaccuum at 0° C. and the peptide was then precipitated and washed with anhydrous ether. After extraction of the peptide from the resin with trifluoroacetic acid, the solvent was evaporated to 15° C. and the peptide was again precipitated with ether. The ether was decanted after centrifugation and the pellet was dissolved in 5% acetic acid with 6 M guanadine HCl.

This solution was desalted on a BioGel P2 column equilibrated in 5% acetic acid and the peptide containing fractions were pooled and lyophilized. A cysteine residue was then added to the carboxyl terminus of the peptide to provide a functional —SH group for the coupling of the peptide to carrier proteins. A

TABLE II

| | Peptide | | | | | |
|---|---|---|---|---|---|---|
| | 1 | 2 | 3 | 4 | 5 | 6 |
| | Residue Nos. | | | | | |
| | 346–357 | 304–321 | 509–526 | 728–752 | 735–752 | 846–860 |
| Sequence | asn | thr | lys | leu | asp | ala |
| | asn[a] | arg | arg | pro | arg | ile |
| | thr | arg | arg | ile | pro | arg[k] |
| | leu | pro | val | pro | glu[i] | his |
| | lys | asn | val | arg | gly | ile |
| | gln | asn | gln | gly | ile | pro[l] |

TABLE II-continued

| Peptide | | | | | |
|---|---|---|---|---|---|
| 1 | 2 | 3 | 4 | 5 | 6 |
| Residue Nos. | | | | | |
| 346–357 | 304–321 | 509–526 | 728–752 | 735–752 | 846–860 |
| ile | thr | arg | pro | glu | arg |
| asp[c] | arg | glu | asp | glu | arg |
| ser[d] | lys | lys | arg | glu | ile |
| lys | ser | arg | pro | gly[j] | arg |
| leu | ile | ala | glu[i] | gly | gln |
| arg | arg[e] | val | gly | glu | gly |
| glu | ile | gly | ile | arg | leu |
| gln | gln[f] | ile[g] | glu | asp | glu |
| phe | arg[f] | gly | glu | arg | arg |
| gly | gly | ala | glu | asp | |
| asn | pro | leu[h] | gly[j] | arg | |
| asn | gly | phe | gly | ser | |
| lys | | | glu | | |
| | | | arg | | |
| | | | asp | | |
| | | | arg | | |
| | | | asp | | |
| | | | arg | | |
| | | | ser | | |

[a]ala in LAV
[b]glu in ARV-2
[c]val in ARV-2; ala in LAV
[d]lys in ARV-2
[e]tyr in ARV-2
[f]omitted in ARV-2
[g]insert val between ile and gly in ARV-2
[h]met in ARV-2
[i]asp in ARV-2
[j]may be asp in HTLV-III
[k]leu in ARV-2
[l]his in ARV-2 glycine residue was added after the cystine to provide a spacer amino acid between the coupled cysteine residue and the amino acid sequences analogous to gp 160. A tyrosine residue was added to the amino terminus for radioactive labelling with $^{125}$Iodine to determine peptide-to-carrier protein coupling efficiency and to identify the peptide during purification by adsorbance at 278 nm.

After desalting on the BioGel P2 column in acetic acid and lyophilization, the peptide was found to have the expected amino acid analysis (see Table II) and eluted as a single peak (92%) on $C_{18}$-reverse-phase HPLC in a linear gradient of 0.05% trifluoacetic acid and 2-propanol.

EXAMPLES 5–9.

Synthesis of Additional Peptides

The method described in Example 4, above, was used to synthesize the Peptides 2–5 listed in Table II, each corresponding to the amino acid sequence of the residues listed.

EXAMPLE 10.

Conjugation of Synthetic Peptide to Carrier

Synthetic peptide 5 (see Table II) was conjugated via the —SH group on the cysteine residue to the amino groups on Keyhole limpet hemacyanin (KLH)(for immunization of rabbits) and the bovine serum albumin (BSA)(for assaying anti-peptide activity) using a heterobifunctional cross-linker, (M-maleimidobenzyl-N-hydroxysuccininmide ester MBS). The details of this method are given at Liu, F.T., et al., 18 Biochemistry 690 (1979) and Green, N. et al., 28 Cell 477 (1982), both of which are hereby incorporated in their entirety by this specific reference thereto. Briefly, 1 mg of either KLH or BSA in 10 mM sodium phosphate, pH 7.2, was incubated with 4 mg and 800 µg of MBS in dimethylformamide, respectively, for thirty minutes at 25° C. Unreaacted MBS and solvent was removed on a Sephadex PD-10 column equilibrated in 50 mM sodium phosphate buffer, pH 6.0. A 100 molar excess of Peptide 5 relative to KLH or BSA, along with approximately 500,000 cpm of $^{125}$[I]labeled Peptide 5 was added to the reaction mixture and incubated an additional three hours at 25° C. Peptide which was not bound to the protein carrier was removed by repeated dialysis. The coupling efficiency was determined by the amount of $^{125}$[I]peptide associated with KLH and BSA and was approximately 62% and 56% for KLH and BSA, respectively.

EXAMPLE 11.

Induction of Immunogenic Response in Rabbits

Two rabbits were each immunized with 100 µg per dose of Peptide 5-KLH complex, prepared as described above, emulsified in Freunds incomplete adjuvant. The rabbits received one intramuscular injection every two weeks, for a total of three injections, and serum was obtained following each immunization.

A solid phase radioimmunoassay was used to titrate the rabbit anti-peptide antisera. Briefly, 200 ng of Peptide 5 coupled to BSA prepared as described in Example 10 was adsorbed to the wells of polyvinyl microtiter plates, and incubated overnight at 4° C. Following the addition of 10% normal goat serum (NGtS) to block nonspecific sites, the rabbit anti-peptide antisera diluted in 10% NGtS was added and incubated 2 hours at 37° C. Antisera was obtained 14 days after each immunization. The microtiter wells were washed with Tween 20 phosphate buffered saline (T-PBS) and $^{125}$[I]goat-anti-rabbit gamma globulin (approximately 500,000 cmp in 50 µl) was added. Following incubation for 1 hour at 37° C., the wells were washed of excess radioactivity with T-PBS, and counted in a gamma counter. All volumes were 50 μl and the anti-peptide titers shown in Table III are expressed as the reciprocal of the endpoint titer dilution (the highest dilution of antisera that gave cpm 5 above the preimmune rabbit sera). The end point titers were based on fivefold dilutions and represent the mean of triplicate values.

TABLE III

| Rabbit | Immunization | Anti-Peptide 5 Titer |
|---|---|---|
| 21 | Pre-immunization | 10 |
|  | Primary | 1250 |
|  | Secondary | 6250 |
|  | Tertiary | 31,250 |
| 22 | Pre-immunization | 10 |
|  | Primary | 1250 |
|  | Secondary | 6250 |
|  | Tertiary | 156,250 |

The results given in Table III show that the two rabbits produced a detectible anti-peptide response (as measured by a peptide-BSA) after a single injection of the peptide-KLH. Serum obtained from each rabbit prior to immunization failed to significantly bind the peptide (titers of less than ten). Anti-peptide titers increased following each injection of the peptide and ranged from 31,250 to 156,250 following the third injection.

The specificity of the antibody response was shown by the inability of the anti-peptide sera to bind the control peptide conjugated to BSA. In addition, the HTLV-III peptide 728-745 (Peptide 5) completely inhibited (100%) the binding of the rabbit anti-peptide to peptide-BSA. The two rabbits also produced high antibody titers to KLH; however, rabbit anti-KLH did not bind peptide-BSA.

EXAMPLE 12.

Recognition of HTLV-III Proteins By Rabbit Anti-Peptide Antibodies.

The ability of the rabbit antibodies to Peptide 5 to recognize the native proteins associated with HTLV-III was examined as follows MOLT-3, an HTLV-III infected T-cell line, was labeled with $^{35}$[S]-cystine and used for immunoprecipitation as described in Example 2, above, to determine whether the anti-peptide sera would bind any radioactively labeled HTLV-III native proteins. The rabbit anti-peptide antibody specifically precipitated a single protein of approximately 160,000 daltons as shown by autoradiographs of SDS-PAGE. This protein is the precursor envelope glycoprotein gp 160 of HTLV-III. No reactivity to HTLV-III proteins was demonstrated when preimmune rabbit sera was used in the immunoprecipitation experiments. The rabbit anti-peptide failed to recognize the gp 120 envelope subunit that is detected with $^{35}$[S]-cystine labeled MOLT-3 cells when human antisera from AIDS patients is used in immunoprecipitation. The gp 41 envelope subunit does not radioactively label to the same degree with $^{35}$[S]-cystine as gp 120 and is difficult to detect by immunoprecipitation.

The difficulty of producing gp 41 at a relatively high level of specific radioactivity was circumvented as follows. HTLV-III infected MOLT-3 cells were double labeled by the addition of both $^{35}$[S]-methionine and $^{35}$[S]-cystine. The glycoprotein populations present in these double cystine-methionine labeled lysates were then enriched by affinity chromatography on lentil-lectin columns as described in Example 2, above. Both gp 160 and gp 41 glycoproteins was observed when the rabbit anti-peptide sera were reacted with these glycoprotein enriched fractions when analyzed by the radioimmunoprecipitation experiment described in Example 2, above.

Western transfer methods for HTLV proteins verified that the rabbit anti-peptide did recognize gp 41. This method uses stock solutions of infected MOLT-3 cell lysates as a source of HTLV-III proteins. In this assay, $5 \times 10^6$ infected cells are solubilized in 1 ml of a 1% Zwittergent 3-14 (Calbiochem-Behring) solution for 5 minutes and centrifugated at $1000 \times g$ for 10 minutes. The resulting supernatant is mixed with an equal volume of disruption buffer (10 mM Tris-HCl, pH 6.8 glycerol and 0.01% bromphenol blue) and boiled for 3 minutes. Eight μl of disrupted cell lysate is electrophoresed in adjacent lanes in 4-25% linear acrylamide gradient gel ($1.5 \times 17 \times 14$ cm) for twenty hours under a constant voltage of 50 V per gel. Electrophoretically separated gradient gels are then transferred to nitrocellulose sheets at 1 amp constant current for 90 minutes at 10° C. using the buffer system described by Towbin, et al., 76 Proc. Natl. Acad. Sci. 4350 (1979), hereby incorporated in its entirety by this specific reference thereto. Pre-stained molecular weight markers (BRL) are also electrophoresed and transferred to nitrocellulose to be used as standards for estimating the molecular weights of the transferred HTLV-III peptides. After the transfer is completed, the nitrocellulose sheets are incubated with 100 ml of 5% w/v non-fat dry milk rehydrated in PBS containing 0.001% w/v methiolate and 0.0001% v/v Antifoam A (Sigma) for 30 minutes at room temperature. Serial dilutions of sera obtained from the rabbits immunized with Peptide 5 were then incubated with the nitrocellulose sheets for 1 hour at 37° C. Nitrocellulose sheets were then washed with 100 ml of PBS-T20. Biotinylated goat anti-human IgG (5 μg/ml) was then incubated with the nitrocellulose sheets for 1 hour at 37° C. in order to detect the binding of the rabbit anti-peptide antibodies. Nitrocellulose sheets were washed again with PBS-T20 followed by the addition of 1 μg/ml of avidin-labeled horse radish peroxidase (AV-HRPO) for 20 min at room temperature. After washing again with PBS-T20, 100 ml of a peroxidase chromagen:substrate solution (0.2 mg/ml of O-dianisdine in PBS plus 1 μl/ml of 30% $H_2O_2$) was added to the nitrocellulose membranes until precipitates were observed on the membrane (10-15 min.). The peroxidase catalyzed reaction terminated by washing the nitrocellulose sheets in 2% SDS in water. Controls for the Western transfer assay include the use of normal human sera and a side by side comparison of the reactivity of the antisera with infected and uninfected cell lysates. Binding with the gp 41 protein was observed, as well as with the gp 120 subunit.

EXAMPLE 13.

Recognition of Synthetic Peptides by Human and Rabbit Antibodies to Viral Causative Agents of AIDS and ARC An enzyme-linked immunosorbent assay (ELISA) may be used for detection of human antibodies against the viral causative agents of AIDS and ARC. Five μg samples of Peptide 5, prepared as described in Example 4 and complexed with BSA as described in Example 10, above, were absorbed to the solid phase of Dynatech Immunolon microtiter wells in borate buffered saline (BBS), pH 8.0, for one hour at 37° C. Nonspecific sites were blocked with 10% normal goat serum (NGtS) in Tween 20 phosphate buffered saline (T-PBS) and then washed with T-PBS.

Figure 4:
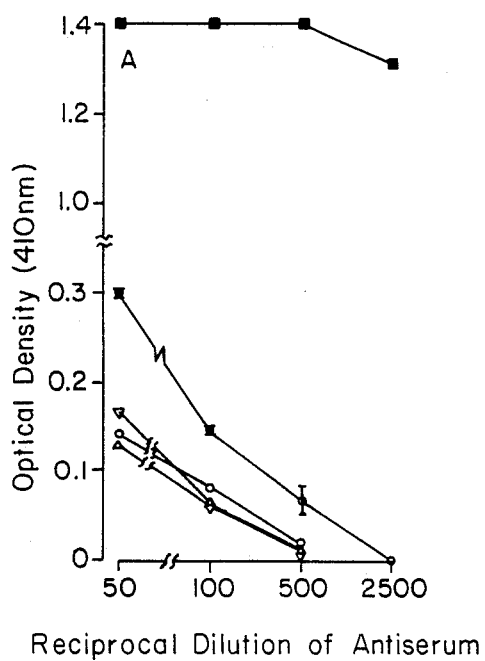
FIG. 4 is a graph of the optical density vs. the reciprocal dilution of the antiserum obtained from rabbits immunized with the gp 120 735–732 (Peptide 5 in Table II) showing the binding of the Peptide 5 by the rabbit antibodies by enzyme linked immunosorbent assay. Data from anti-peptide serum are represented by a ( ) and preimmune rabbit serum are represented by a (o). Data from human AIDS serum, and control serum no. 1 and control serum no. 2 are represented by a ( ), ( ), and ( ), respectively.

Human and rabbit sera diluted in 10% NGtS was then added to the Peptide 5-coated plates and incubated for one hour at 37° C., followed by washing with T-PBS. Biotin goat anti-human IgG or biotin goat anti-rabbit IgG (Vector Laboratories, Burlingame, CA) was then incubated with the bound human and rabbit sera, respectively, for one hour at 37° C. The wells were then washed and avidin conjugated to horseradish peroxidase (Av-HRP) was added for 20 minutes at room temperature. The wells were then washed with T-PBS to remove any unbound Av-HRP and peroxidase activity was determined using a 1 mM solution of 1,2$^1$-azino-di(3-ethyl-benzthiazoline-sulfonic acid) (Sigma Chemical Co.) and 0.03% $H_2O_2$ as substrate. The reaction was stopped with 5% (w/v) sodium dodecyl sulfate in water prior to quantitating spectrophotometrically at 410 nm using a Dynatech plate reader. Optimal dilutions of each reagent were selected by titration. All reagents for determining specific binding except the substrate were diluted in 10% NGtS. The results are shown in FIG. 4, in which the individual sera are depicted as follows: rabbit anti-peptide serum (■); preimmune rabbit serum (o); human AIDS serum (●); control serum #1 (▽); and control human serum #2 (△). All tests were performed in triplicate and the backets refer to the range of values.

EXAMPLE 14.

Assay for Diagnosis of AIDS or ARC: Detection of Antibodies

An insoluble support matrix is coated with 5 ug each of the peptide-BSA complexes prepared as described above in Example 10 in borate buffer saline (BBS), pH 8.0, for 8 hours at 4° C. (Alternatively, the matrix may be coated for one hour at 37° C.). The peptide-BSA is blocked for 20 minutes with 10% normal goat serum (NGtS), and washed three times with Tween 20 phosphate buffered saline (T-PBS). A serum sample suspected of containing antibody to the AIDS virus is added and incubated for one hour at 37° C. The support matrix is washed three times with T-PBS, and biotin-labeled goat anti-human Ig (1:1000 of 5 mg/ml in 10% NGtS, Vector Labs, Burlingame, Calif.) is added. The matrix is washed three times with T-PBS, and a 1:2000 of 5 mg/ml avidin-horseradish peroxidase is added and incubated for twenty minutes at room temperature. The matrix is washed three times with T-PBS and the substrate, the diammonium salt of 2, 2'-azinodi-(3-ethyl-benzthiazoline sulfonic acid) (ABTS) with $H_2O_2$, is added. The enzyme reaction is stopped with 10% SDS and optical density is read at 410 nm as described in Example 13.

EXAMPLE 15.

Assay for Diagnosis of AIDS or ARC: Detection of Antigen

To detect the presence of the AIDS antigen, the solid phase matrix is coated with antibodies produced by immunization with synthetic peptides 1-6, and the antibodies blocked and washed as described above. The biological fluid sample suspected of containing the AIDS or ARC viral causative agent is then added and washed. The assay can be conducted either as a direct binding assay or as an inhibition assay. If a direct binding assay is conducted, biotin-labeled antibodies to the AIDS and/or ARC virus produced as described above are added and washed. The avidin-labeled enzyme is then added as described above and washed, and the substrate is added as described above. The reaction is stopped and the optical density is read.

If conducted as an inhibition assay, instead of adding biotin-labeled antibody to AIDS virus, the biotin-labeled synthetic peptide is added and the insoluble support matrix is washed. The avidin-labeled enzyme is then added and washed. The substrate is added, the reaction stopped and optical density is read. The IgG from human or chimpanzee AIDS-containing serum is purified by ion exchange chromotography on a Whatman DE-52 anion exchange column. IgG from rabbit anti-peptide is purified with a protein A-Sepharose 4B column (Pharmacia). The IgG is biotinylated using biotin-N-hydroxysuccinamide ester (Boehinger Manheim).

EXAMPLE 16.

Vaccination Against AIDS and ARC

To vaccinate a subject against the viral causative agents of AIDS and ARC, the synthetic peptides 1-6 are coupled to a carrier as described in Example 10, above. The synthetic peptide-carrier complexes are injected into the subject in a bolus of between 100 to 1000 μg of synthetic peptides in alum as an adjuvant. Three separate injections may be given, either intramuscularly or subcutaneously, on a biweekly basis until a measurable antibody response to the virus is detected. Other time intervals such as 0, 1 and 6 months may also be used for the injection of the synthetic peptide.

EXAMPLE 17.

Screening of Putative AIDS Vaccines

The synthetic peptide of the present invention may also be used to screen potential AIDS vaccine candidates for their ability to induce an immunogenic response in an animal subject. The synthetic peptides (or the synthetic peptides coupled to a carrier) are coated onto the insoluble matrix as described above in Example 7. The vaccine candidate is then incubated with antibodies against the peptide (with or without biotin labelling). If biotin labeled, the avidin-enzyme is added, if not, a biotin anti-species antibody such as biotin goat anti-rabbit IgG is added, followed by the addition of the avidin-enzyme. The substrate is added, the reaction stopped and optical density read to determine the ability of the vaccine candidate to block the binding of the peptide.

The preceding examples are presented by way of exemplification only and not by limitation. Variations in these methods will be known to those skilled in the art, and it is expected that all such variations will be made without departing from the spirit and scope of the present invention as claimed in the following claims.

We claim:

1. A synthetic peptide having the following amino acid sequence: asn-a-thr-leu-b-gln-ile-c-d-lys-leu-arg-glu-gln-phe-gly-asn-asn-lys; where a is asn or ala; b is lys or glu; c is asp, val or ala; and d is ser or lys.

2. A synthetic peptide having the following amino acid sequence: thr-arg-pro-asn-asn-asn-thr-arg-lys-ser-ile-e-ile-f-f-gly-pro-gly; where e is arg or tyr; and f is either gln, arg, or omitted.

3. A synthetic peptide having the following amino acid sequence: lys-arg-arg-val-val-gln-arg-glu-lys-arg-ala-val-gly-g-ile-gly-ala-h-phe; where g is val or omitted; and h is leu or met.

4. A synthetic peptide having the following amino acid sequence: x-asp-arg-pro-i-gly-ile-glu-glu-glu-j-gly-glu-arg-asp-arg-asp-arg-ser; where x is leu-pro-ile-pro-arg-gly-pro or omitted; i is glu or asp; and j is gly or asp.

5. A synthetic peptide having the following amino acid sequence: ala-ile-k-his-ile-l-arg-arg-ile-arg-gln-gly-leu-glu-arg; where k is arg or leu; and l is pro or his.

6. An immunogenic composition comprising a carrier conjugated to a synthetic peptide selected from the group consisting of the following amino acid sequences:

asp-arg-pro-glu-gly-ile-glu-glu-glu-gly-glu-arg-asp-arg-asp-arg-ser;

asp-arg-pro-glu-gly-ile-glu-glu-asp-gly-glu-arg-asp-arg-asp-arg-ser; and asp-arg-pro-asp-gly-ile-glu-glu-glu-gly-glu-arg-asp-arg-asp-arg-ser.

7. An antibody raised against a synthetic peptide as claimed in any one of claims 1–5.

8. A method for the detection of antibodies against the viral causative agents of AIDS comprising contacting a synthetic peptide as claimed in any one of claims 1–5 with a sample suspected of containing said antibodies and using the binding affinity of the synthetic peptide to detect said antibodies.

* * * * *